US009389180B2

(12) United States Patent
Chilese et al.

(10) Patent No.: US 9,389,180 B2
(45) Date of Patent: Jul. 12, 2016

(54) METHODS AND APPARATUS FOR USE WITH EXTREME ULTRAVIOLET LIGHT HAVING CONTAMINATION PROTECTION

(71) Applicant: KLA-Tencor Corporation, Milpitas, CA (US)

(72) Inventors: Francis C. Chilese, San Ramon, CA (US); John R. Torczynski, Albuquerque, NM (US); Rudy Garcia, Union City, CA (US); Leonard E. Klebanoff, Dublin, CA (US); Gildardo R. Delgado, Livermore, CA (US); Daniel J. Rader, Albuquerque, NM (US); Anthony S. Geller, Albuquerque, NM (US); Michail A. Gallis, Albuquerque, NM (US)

(73) Assignees: KLA-Tencor Corporation, Milpitas, CA (US); Sandia Corporation, Albuquerque, NM (US)

( * ) Notice: Subject to any disclaimer, the term of this patent is extended or adjusted under 35 U.S.C. 154(b) by 109 days.

(21) Appl. No.: 14/176,587

(22) Filed: Feb. 10, 2014

(65) Prior Publication Data
US 2014/0231659 A1    Aug. 21, 2014

Related U.S. Application Data

(60) Provisional application No. 61/765,143, filed on Feb. 15, 2013.

(51) Int. Cl.
*G01J 1/42* (2006.01)
*G01N 21/59* (2006.01)
*G03F 7/20* (2006.01)

(52) U.S. Cl.
CPC ............ *G01N 21/59* (2013.01); *G03F 7/70933* (2013.01)

(58) Field of Classification Search
CPC .................................................. G03F 7/70916
USPC .............................. 250/492.2, 372
See application file for complete search history.

(56) References Cited

U.S. PATENT DOCUMENTS 6,153,044 A    11/2000    Klebanoff et al.
6,369,874 B1 *  4/2002    del Puerto ........... G03F 7/70933
                                                      250/492.2

(Continued)

FOREIGN PATENT DOCUMENTS

JP    2010212674    9/2010
KR    1020090133000    12/2009

OTHER PUBLICATIONS

International Search Report and Written Opinion regarding PCT/US2014/015791 dated May 26, 2014.

(Continued)

*Primary Examiner* — David Porta
*Assistant Examiner* — Abra Fein
(74) *Attorney, Agent, or Firm* — Simpson & Simpson, PLLC

(57) ABSTRACT

An apparatus for use with extreme ultraviolet (EUV) light comprising A) a duct having a first end opening, a second end opening and an intermediate opening intermediate the first end opening the second end opening, B) an optical component disposed to receive EUV light from the second end opening or to send light through the second end opening, and C) a source of low pressure gas at a first pressure to flow through the duct, the gas having a high transmission of EUV light, fluidly coupled to the intermediate opening. In addition to or rather than gas flow the apparatus may have A) a low pressure gas with a heat control unit thermally coupled to at least one of the duct and the optical component and/or B) a voltage device to generate voltage between a first portion and a second portion of the duct with a grounded insulative portion therebetween.

29 Claims, 5 Drawing Sheets

(56) References Cited

U.S. PATENT DOCUMENTS

| | | | |
|---|---|---|---|
| 6,533,952 | B2 | 3/2003 | Klebanoff et al. |
| 7,159,719 | B2 | 1/2007 | Golda |
| 7,297,895 | B2 | 11/2007 | Allen |
| 7,623,239 | B2 | 11/2009 | Fielden et al. |
| 7,911,598 | B2 | 3/2011 | Kraus et al. |
| 2005/0083515 | A1 | 4/2005 | Naulleau |
| 2006/0017895 | A1 | 1/2006 | Sogard |
| 2006/0175558 | A1* | 8/2006 | Bakker .............. G03F 7/70175 250/492.2 |
| 2006/0192158 | A1 | 8/2006 | Wedowski et al. |
| 2011/0239738 | A1 | 10/2011 | Bisschops et al. |
| 2012/0229783 | A1 | 9/2012 | Nienhuys et al. |
| 2013/0264494 | A1 | 10/2013 | Subrahmanyan et al. |
| 2013/0313442 | A1 | 11/2013 | Wang et al. |

OTHER PUBLICATIONS

Goldstein, Joseph, I., D.E. Newbury, P. Echlin, D.C. Joy, A.D. Romig Jr., C.E. Lyman, C. Fiori, and E. Lifshin, "Scanning Electron Microscopy and X-ray Microanalysis", 2nd Edition, 1992, p. 514-515, Plenum Press, New York, Gallis, M. A., J. R. Torczynski, and D. J. Rader, "Nanoparticle Knudsen Layers in Gas-Filled Microscale Geometries", Physical Review E, vol. 77, paper 036302, 2008.

Bird, G.A., "Molecular Gas Dynamics and the Direct Simulation of Gas Flows", Clarendon Press, updated, 1998, pp. 429, Oxford, UK.

COMSOL Multiphysics User's Guide, "The Chemical Engineering Module", Version 3.5a, COMSOL AB, Stockholm, Sweden, 2008; http://www.comsol.com/, 2013, pp. 13.

Ennos, A. E., "The sources of electron-induced contamination in kinetic vacuum systems", British Journal of Applied Physics, vol. 5, No. 3, pp. 27-31, 1954.

Friedlander, Sheldon, K., "Smoke, Dust, and Haze: Fundamentals of Aerosol Dynamics", Second Edition, 2000, p. 41, Oxford University Press, New York, NY.

Gallis, M. A., J. R. Torczynski, and D. J. Rader, "An Approach for Simulating the Transport of Spherical Particles in a Rarefied Gas Flow via the Direct Simulation Monte Carlo Method," Physics of Fluids, vol. 13, No. 11, pp. 3482-3492, 2001.

Gallis, M. A., J. R. Torczynski, and D. J. Rader, "Nonzero-Concentration Boundary Condition for Advection-Diffusion Aerosol-Transport Modeling", Aerosol Science and Technology, vol. 42, pp. 829-831, 2008.

LBL/CXRO, 2010: Lawrence Berkeley National Laboratory, Center for X-Ray Optics (CXRO), http://www.cxro.lbl.gov.

Lide, Ph.D., David R., CRC Handbook of Chemistry and Physics, 88th edition, CRC Press, Taylor & Francis Group, pp. 1-1, 2008, Boca Raton, FL.

Mott, 2012: Mott Corporation, http://www.mottcorp.com/, "Porous Metal Overview," http://www.mottcorp.com/media/media_overview.cfm/, 2012.

Reid, Robert C., J. M. Prausnitz, and B. E. Poling, "The Properties of Gases and Liquids", Fourth Edition, McGraw-Hill Book Company, Table II-2, 1987, New York, NY.

http://henke.lbl.gov/optical_constants/filter2.html, printed 2014.

\* cited by examiner

METHODS AND APPARATUS FOR USE WITH EXTREME ULTRAVIOLET LIGHT HAVING CONTAMINATION PROTECTION

CROSS REFERENCE TO RELATED APPLICATIONS

This patent application claims priority of U.S. Provisional Patent Application No. 61/765,143 filed Feb. 15, 2013, by Chilese et al. and titled "Protective Tower to Keep Surfaces Free of Particulate and Molecular Contamination (Method, Hardware, Design)." Said application is incorporated herein by reference.

STATEMENT REGARDING FEDERALLY SPONSORED RESEARCH OR DEVELOPMENT

This invention was developed with government support under Cooperative Research and Development Agreement No. SC11/01785.00 awarded by Sandia Corporation (a wholly-owned subsidiary of Lockheed Martin Corporation) as operator of Sandia National Laboratories under its U.S. Department of Energy Contract No. DE-AC04-94AL85000. The government has certain rights in the invention.

FIELD OF THE INVENTION

The present invention relates to apparatus and methods for reducing contaminants in an extreme ultraviolet system.

BACKGROUND OF THE INVENTION

Apparatus for reducing contamination in apparatus using deep ultraviolet (UV) light (e.g., having a 193 nm wavelength) such as actinic mask inspection systems or deep UV lithographic systems are known. Since these systems operate at atmospheric pressures, ventilation systems relying on the flow of air at atmospheric pressure have been used to reduce the effects of contaminants.

By contrast, extreme ultraviolet (EUV) light (e.g., having a 13.5 nm wavelength) actinic mask inspection systems or EUV lithographic systems operate in vacuum or near-vacuum conditions because EUV light is not sufficiently transmitted by air at atmospheric pressure. Accordingly, conventional contamination control systems using a flow of air are not suitable for EUV systems.

Various contamination protection apparatus for use with EUV light have been proposed but have had only limited success. For example, contamination protection using vacuum pumping has been proposed but has not been adequate and has not been capable of providing protection in areas in close proximity to optical components, such as near surfaces of optics, masks or detectors. Another proposed apparatus uses cross-flow gas jets. Such systems use high-speed gas flow directed nominally parallel to a surface of a component to blow away or deflect contaminants; however the high speed flow of gas can produce density gradients that degrade the imaging performance of a subject optical system.

SUMMARY OF THE INVENTION

A first aspect of the invention is directed to an apparatus for use in an extreme ultraviolet (EUV) actinic mask inspection system or an EUV lithographic system, the apparatus having contamination protection and comprising A) a duct having a first end opening, a second end opening and an intermediate opening disposed intermediate the first end opening the second end opening, B) an optical component disposed so as 1) to receive EUV light from first end opening after the light has passed through second end opening or 2) to send light through the first end opening to the second end opening, and C) a source of low pressure gas at a first pressure, the gas having a high transmission of EUV light, fluidly coupled to the intermediate opening, the first end opening and the second end opening maintained at a lower pressure than the first pressure.

In some embodiments, one of the duct and the optical component are thermally coupled to a heat control unit, to maintain the duct at a lower temperature than the optical component. In some embodiments, a first portion of the duct is thermally coupled to a heat control unit, to maintain a temperature gradient between the first portion of the duct and a second portion of the duct.

A gas permeable material may be disposed at the intermediate opening. The intermediate opening may be disposed closer the first end opening than the second end opening.

The optical component may comprise one of a mirror, a reticle, a sensor, a lens or a filter. In some embodiments, the optical component is disposed remote from the first end opening.

The low pressure gas may have a transmission rate greater than 70% for the EUV light. The first pressure may be less than 0.01 atmospheres. The gas may comprise molecular Hydrogen or Helium.

In some embodiments, the length of the duct is at least two times greater than the maximum width dimension of a duct cross section.

The apparatus may be in a combination with at least one second duct having a second-duct first end opening, a second-duct second end opening and a second-duct intermediate opening. The second-duct intermediate opening is disposed intermediate the second-duct first end opening and the second-duct second end opening. The optical component is disposed so as 1) to receive light from second-duct first end opening after the light has passed through second-duct second end opening or 2) to send light through the second-duct first end opening to the second-duct second end opening. The apparatus further comprises a second-duct source of low pressure gas at a second-duct first pressure, the second-duct gas having a high transmission of EUV light, fluidly coupled to the second-duct intermediate opening. The second-duct first end opening and the second-duct second end opening are maintained at a lower pressure than the second-duct first pressure.

The source of low pressure and the second-duct source of low pressure may be the same source, and the gas and the second-duct gas are the same gas.

The duct may be thermally coupled to the heat control unit, the heat control unit adapted to maintain the duct at a cooler temperature than the optical component.

In some embodiments, the apparatus further comprises a voltage device adapted to generate a voltage between a first portion of the duct and a second portion of the duct with a grounded electrically-insulative portion therebetween.

Another aspect of the invention is directed to an apparatus for use in an extreme ultraviolet (EUV) actinic mask inspection system or an EUV lithographic system, the apparatus having contamination protection and comprising A) a duct having a first end opening, a second end opening and an intermediate opening disposed intermediate the first end opening the second end opening, B) an optical component disposed so as 1) to receive light from first end opening after the light has passed through second end opening or 2) to send light through the first end opening to the second end opening, and C) a heat control unit thermally coupled to at least one of the duct and the optical component. In some embodiments, the average temperature gradient between the duct and the optical component is at least 10 degrees Celsius per centimeter.

The duct may be thermally coupled to the heat control unit, the heat control unit adapted to maintain the duct at a cooler temperature than the optical component.

The first portion of the duct may be thermally coupled to a heat control unit to maintain a temperature gradient between the first portion of the duct and a second portion of the duct. In some embodiments, the average temperature gradient is at least 10 degrees Celsius per centimeter.

Another aspect of the invention is directed to an apparatus for use in an extreme ultraviolet (EUV) actinic mask inspection system or an EUV lithographic system, the apparatus having contamination protection and comprising A) a duct having a first end opening, and a second end opening, B) an optical component disposed so as 1) to receive light from first end opening after the light has passed through second end opening or 2) to send light through the first end opening to the second end opening, and C) a voltage device adapted to generate a voltage between a first portion of the duct and a second portion of the duct with a grounded insulative portion therebetween.

Yet another aspect of the invention is directed to a method of contamination protection for use in an extreme ultraviolet (EUV) actinic mask inspection system or an EUV lithographic system, comprising I) flowing a low pressure gas in a duct having A) a first end opening and a second end opening and B) an intermediate opening disposed intermediate the first end opening the second end opening, and II) projecting EUV light through the duct, the EUV light 1) traveling from the second end opening then through the first end opening to an optical element or 2) traveling from the optical component, then through the first end opening to the second end opening, the gas having a high transmission of EUV light.

The optical component may comprise one of a mirror, a reticle, a sensor, a lens or a filter. In some embodiments, the optical component is disposed remote from the first end opening. The low pressure gas may have transmission rate greater than 70% for the EUV light. The low pressure gas may have a pressure of less than 0.01 atmospheres. The gas may comprise molecular Hydrogen or Helium.

Still another aspect of the invention is directed to a method of contamination protection for use in an extreme ultraviolet (EUV) actinic mask inspection system or an EUV lithographic system, comprising A) maintaining a voltage difference between a first portion of a duct and a second portion of the duct with a grounded insulative portion disposed between the first portion and the second portion, the duct having A) a first end opening and a second end opening, the first portion and second portion both being disposed between the first end opening and the second end opening and B) projecting EUV light through the duct, the EUV light 1) traveling from the second end opening then through the first end opening to an optical element or 2) traveling from the optical component, then through the first end opening to the second end opening, the gas having a high transmission of EUV light.

The method may further comprise providing a gas in the duct, the gas having a high transmission of EUV light.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1A:
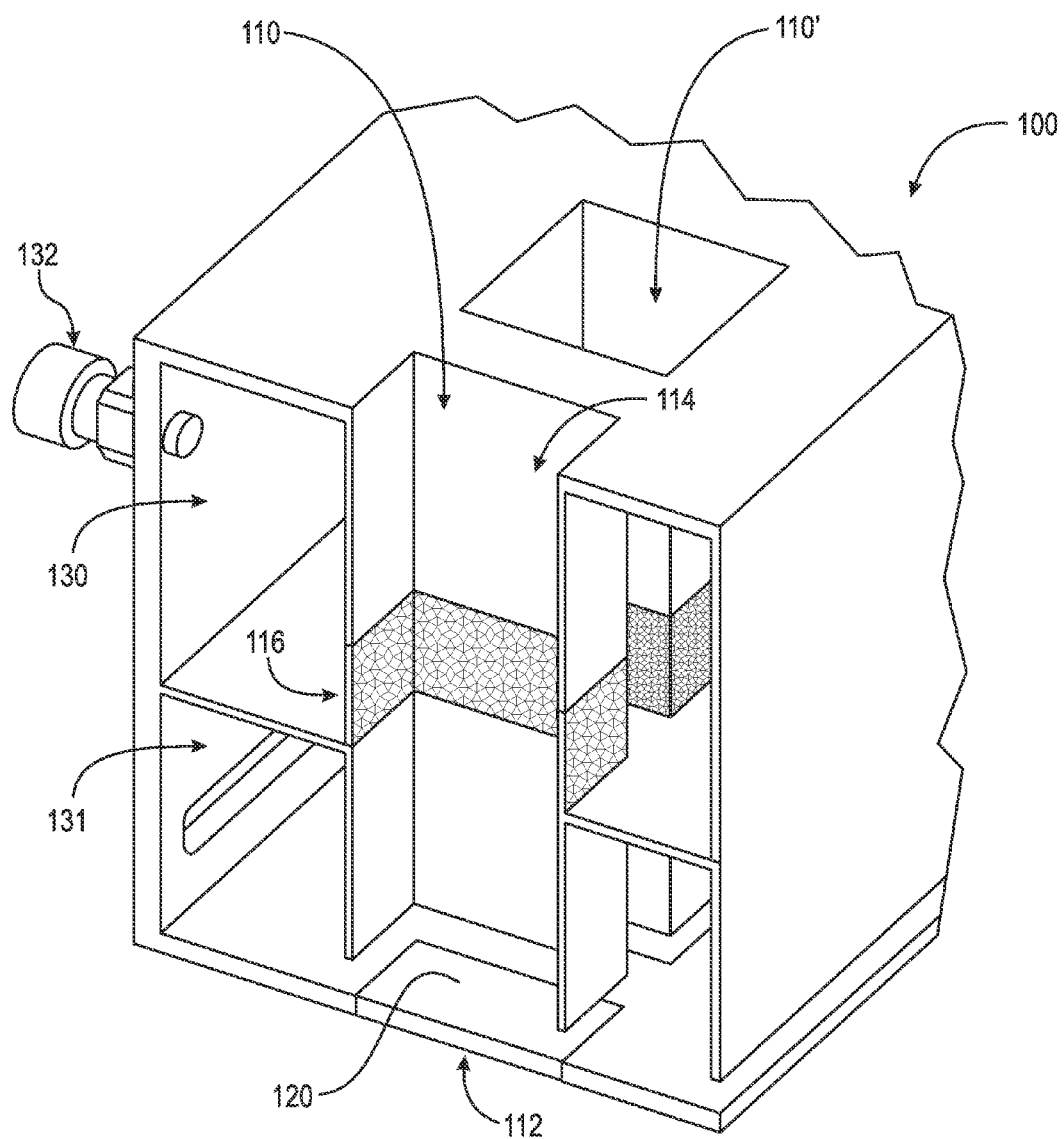
FIG. 1A is a partial, projection view of an example of an embodiment of an apparatus for use in an extreme ultraviolet (EUV) actinic mask inspection system or an EUV lithographic system, the apparatus having contamination protection according to aspects of the present invention.

In the following description, numerous specific details are set forth in order to provide a thorough understanding of aspects of the present invention. The aspects of the present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Same reference numerals refer to the same elements throughout the various figures. Furthermore, only reference numerals necessary for the description of the respective figure are shown in the figures. The shown embodiments represent only examples of how the invention can be carried out. This should not be regarded as limiting the invention.

Aspects of the present invention are directed to apparatus to provide protection to components of an extreme ultraviolet (EUV) actinic mask inspection system or an EUV lithographic system and to enhance performance of said system by reducing or eliminating contaminants that are commonly encountered during use of said system. The apparatus contains a duct through which a low pressure gas is flowed. By sweeping the contaminants from the duct (i.e., removing the contaminants by use of flowing gas) or sweeping the contaminants before entry into the duct, the contaminants are reduced in amount or prevented from landing on optical surfaces or other operational surfaces of the systems. For example, contaminants may include water vapor or hydrocarbons from various adhesives in the components or particulate matter.

Figure 1B:
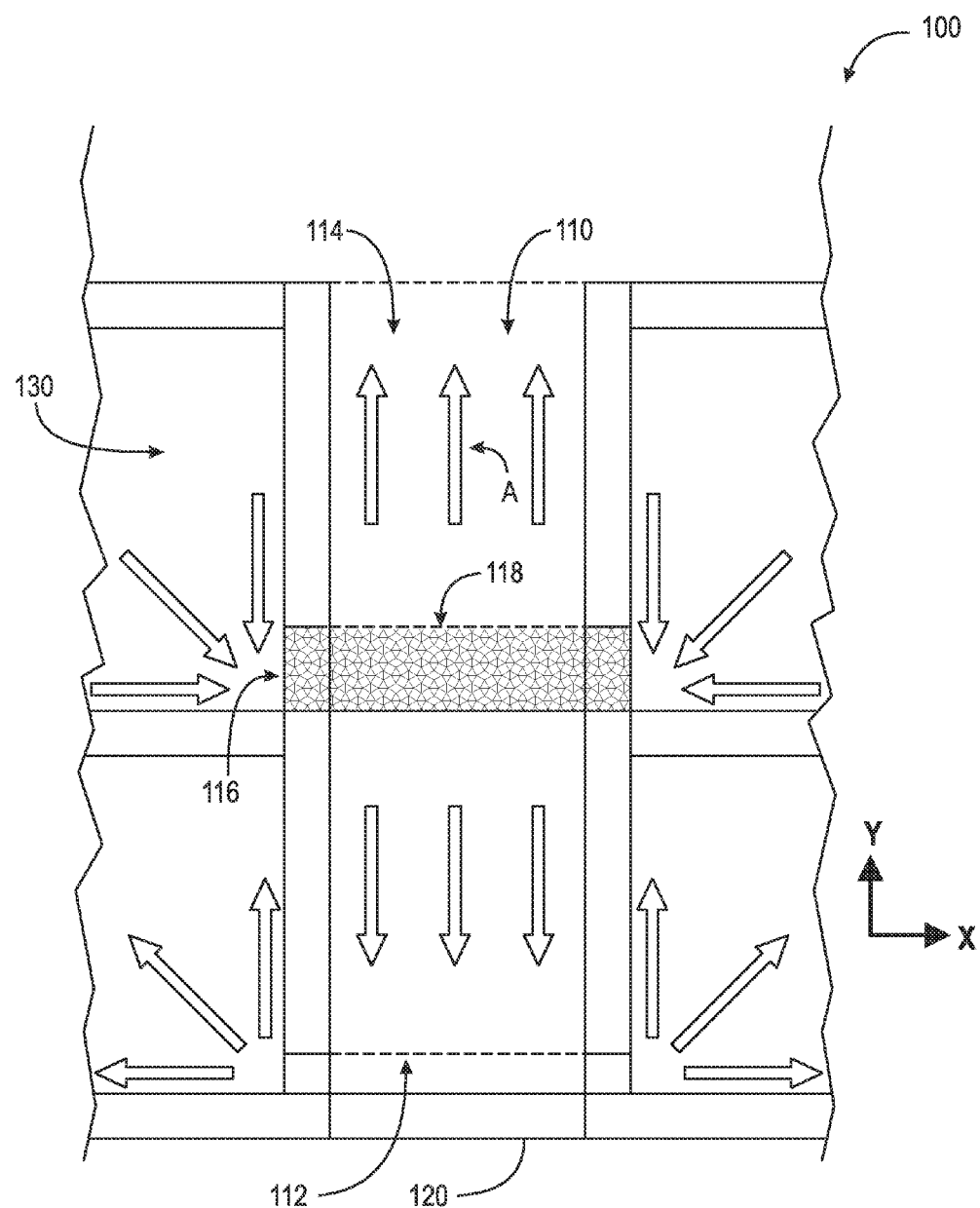
FIG. 1B is a partial, schematic diagram of the apparatus of FIG. 1A.

An example of an embodiment of an apparatus 100 having contamination protection according to aspects of the present invention is discussed below with reference to FIGS. 1A and 1B. It is to be appreciated that the apparatus can be used in an extreme ultraviolet (EUV) actinic mask inspection system or an EUV lithographic system. FIG. 1A is a partial, projection view of apparatus 100 with a first duct 110 shown in cutaway and only an end opening of duct 110' (which is constructed the same as duct 110) is visible; and FIG. 1B is a schematic diagram of apparatus 100.

Apparatus 100 comprises a duct 110, an optical component 120 and a source of low pressure gas 130.

Duct 110 has a first end opening 112, a second end opening 114 and a intermediate opening 116 disposed intermediate the first end opening the second end opening. In the illustrated embodiment, duct 110 has a cross-section shape that is square; however, the duct may have any suitable cross-sectional shape. For example, the cross-sectional shape may be chosen to facilitate the transmission of light through the duct to and/or from optical component 120, or to facilitate the flow of gas toward and/or away from the optical component 120. The cross-sectional shape may change along the length of the duct (i.e., along the y axis). In some embodiments, there are no other openings in duct 110 other than first end opening 112, second end opening 114 and intermediate opening 116.

Intermediate opening 116 may extend around the entire circumference of the duct (as in the illustrated embodiment) or only a portion thereof.

Duct 100 may be constructed of any suitable materials to facilitate transmission of light and gas therethrough. Typically, the duct is made of material that is rigid and non-permeable to the gas provided by source 130. Typically, the first end opening 112 and the second end opening 114 are free of any substance so as to facilitate the transmission light and the flow of air along the duct. In some embodiments, a gas permeable material 118 is provided at intermediate opening 116 to modify the air flow through the intermediate opening (e.g., to improve uniformity of the flow of gas in the duct) or to filter the air prior to entering the duct. For example, the gas permeable material may comprise a sintered porous plate from the Mott Corporation of Farmington, Conn. In the illustrated embodiment, the plate is comprised of 4 plates one on each side of the duct and covers the intermediate opening at all locations around the circumference of the duct, but may have any suitable shape and may comprise one or more pieces. For example, the pores in the plate may be in the range of 0.1-100 microns in diameter.

It will be appreciated that the position of intermediate opening 116 may be selected to be closer to optical component 120 or further from optical component 120 depending on the amount and types of anticipated contaminants entering the first end opening and the second end opening. It will be appreciated that the closer intermediate opening 116 is located to optical component 120 the greater the protection from contaminants coming from second end 114 and the closer intermediate opening 116 is located to the second end opening 114 the greater the protection from contaminants coming from the first end opening 112 such as from optical component 120.

Optical component 120 is disposed so as 1) to receive light from first end opening 112 after the light has passed through second end opening 114 or 2) to send light through the first end opening 112 and through the second end opening 114. Optical component 120 may be arranged relative to first end opening 112 in any manner so as to operatively receive and/or send light through second opening 114. For example, optical component 120 may be a mirror, a reticle (also commonly referred to as a mask), a sensor, a lens or a filter arranged to operatively receive the light. Typically, the light is directed through the duct without impinging on the walls of the duct.

Optical component 120 may be located at first end opening 112 or remote from first end opening 112 at a location outside of the duct provided the optical component is arranged to operatively receive and/or send light projected through second end opening 114.

Source of low pressure gas 130 provides a gas at a first pressure and is fluidly coupled to intermediate opening 116. First end opening 112 and second end opening 114 are maintained at a lower pressure than the first pressure to achieve a flow of the gas from intermediate opening 116 to the first end opening 112 and second end opening 114. Arrows A show the direction of gas flow. The gas is selected to have a high transmission of EUV light.

The source 130 may comprise any suitable container for maintaining low pressure gas prior its entry into duct 110. For example, the source may comprise a tank and/or plenum filled with the low pressure gas through an inlet 132.

It will be appreciated that the low pressure gas entering duct 110 at the intermediate opening 116 will have a flow pattern that is bifurcated with a first portion of the gas flowing toward the first end opening 112 (e.g., into an outlet plenum 131) and a second portion of the gas flowing toward the second end opening 114. The first portion of gas will eliminate or reduce the contaminants entering duct 110 from the first end opening 112 and the second portion of gas will eliminate or reduce the contaminants entering the duct from the second end opening 114. Typically, gas exits first end opening 112 flowing primarily in a direction parallel to the y axis; typically, gas exiting second end opening 114 flows primarily in a direction parallel to the y axis.

It will be appreciated that the gas should be selected such that it operates to sweep out contaminants that enter the duct from the first end opening 112 and the second end opening 114 or prevent contaminants from entering duct 110, and the gas should be selected to allow an adequate transmission rate of the EUV light through duct 110. It will also be appreciated that while, for a given duct cross-sectional area, a longer duct length will provide a greater ability to sweep out contaminants, a longer duct will also have a decreased transmission rate of the EUV light.

An appropriate gas is selected according to its optical properties and should have an appropriate pressure. The percent transmission of EUV light from first end opening 112 to second end opening 114 is typically greater than 50%, and in some instance greater than 70%, and in other instances greater than 90%. The term "high transmission of EUV light" is defined herein to mean greater than or equal to 50% transmission of EUV light. An appropriate transmission rate and sweeping ability are typically achieved at pressures less than 0.1% of an atmosphere and in some instances less than 0.01% of an atmosphere. The term "low pressure gas" is defined herein to mean less than 0.1% of an atmosphere.

Gases having suitable transmission rates of EUV light at a pressure suitable to sweep contaminants include molecular Hydrogen and Helium.

As indicated above, for a given duct cross-section, a longer duct provides greater contamination protection. In many instances, the maximum length of duct 110 is determined by the space available within the optical system in which apparatus 100 is to be used. Typically the length of the duct is selected to be at least 2 times greater than the maximum width dimension of the duct cross-section. In some instances, the length is at least 20 times greater than the maximum width dimension of the duct cross-section and may reach 200 time greater than the maximum width dimension of the of the duct cross-section. Excluding spatial constraints, the maximum length will typically be determined by the resistance to gas flow resulting from the longer duct length.

The ability of the above-described apparatus to provide contaminant control is determined, at least in part, by a given contaminant's diffusivity in the gas (e.g., as determined by gas pressure and mass density), the flow rate of the low pressure gas, and the distance from the intermediate opening 116 to a given end opening 112, 114. Accordingly, a given protection from contaminants can be selected by choosing suitable values for the identified parameters.

It will be appreciated that, in FIG. 1A, the projection view shows that one or more additional ducts (e.g., duct 110') may be included in the apparatus to form an array of ducts. The ducts may be connected to common plenums or two or more separate plenums. An advantage of an array of ducts is that a larger optical component area can be protected from contamination while maintaining a suitable length to width ratio (as set forth above) for each duct in the array. The array can have any suitable configuration of ducts so as to minimize the impact of the non-transmitting portions between the ducts.

Figure 2:
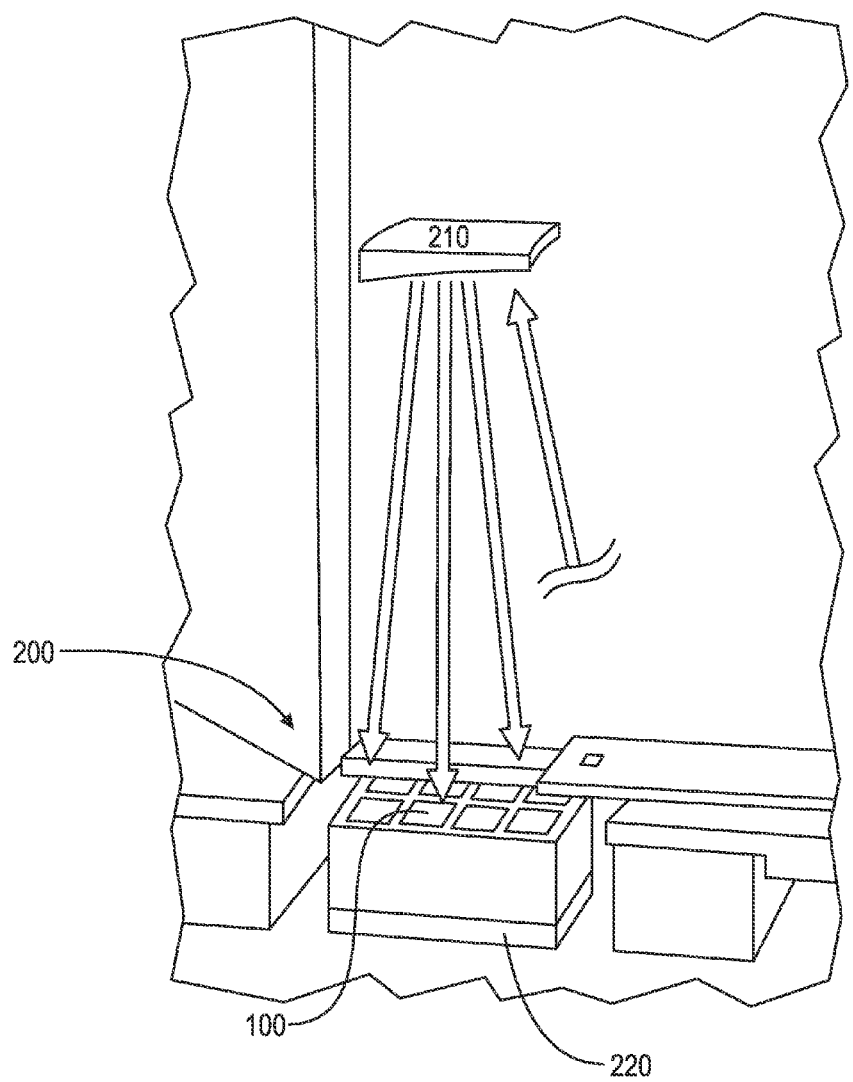
FIG. 2 is a partial, schematic diagram of an example of an array of the apparatus of FIG. 1A operatively disposed within an example of a mask inspection system.

FIG. 2 is a partial, schematic diagram of an example of an array of ducts 200 including the apparatus 100 of FIG. 1A that is operatively disposed within an example of a mask inspection system. To avoid obfuscation, only a single mirror 210 of an optical system that projects light though the array of ducts onto a light sensor 220 (e.g., a Time Delay Integration sensor (TDI)) is shown. Although only a single mirror is shown, an optical system may have one or more reflective or transmission elements to project light though the ducts.

An apparatus providing contamination protection for use in an extreme ultraviolet (EUV) actinic mask inspection system or an EUV lithographic system such as those described above can be provided with thermophoretic contamination protection. As set forth below, in such systems, a temperature gradient is established to selectively direct contaminants away from selected components within the apparatus.

Figure 3A:
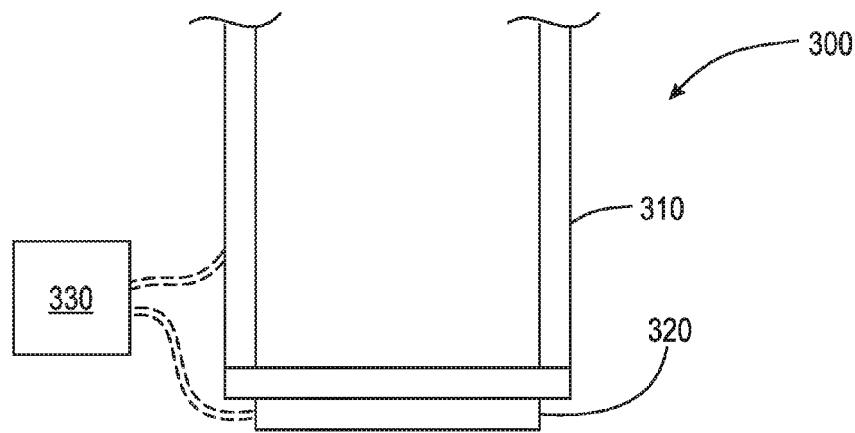
FIG. 3A is a partial, schematic, cross-sectional diagram of an example of an embodiment of an apparatus for use in an extreme ultraviolet (EUV) actinic mask inspection system or an EUV lithographic system, the apparatus having contamination protection including thermophoretic protection according to aspects of the present invention.
Figure 3B:
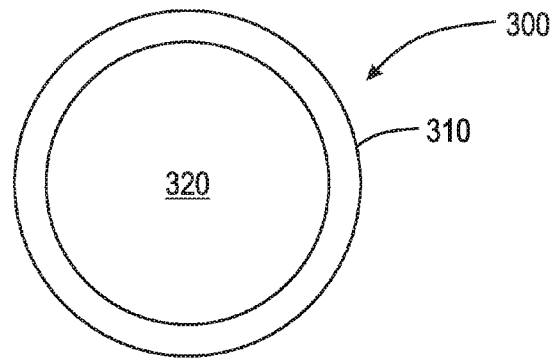
FIG. 3B is a top view of the apparatus of FIG. 3A.

An example of an embodiment of an apparatus 300 for use in an extreme ultraviolet (EUV) actinic mask inspection system or an EUV lithographic system is described below with reference to FIGS. 3A and 3B, where FIG. 3A is a partial, schematic, cross-sectional diagram of the apparatus and FIG. 3B is a top view of the apparatus of claim 3A. Apparatus 300 has contamination protection including thermophoretic protection according to aspects of the present invention. FIG. 3A or illustrates a bottom portion of a duct 300.

While a gas is needed to achieve thermophoretic effects, the gas need not flow. Accordingly, apparatus having thermophoretic capabilities may but need not have components needed for a gas to flow. Portions of the apparatus described above with reference to FIGS. 1A, 1B and 2 are omitted to facilitate discussion.

It will be appreciated that, by maintaining a temperature gradient between a first portion of the apparatus and a second portion of the apparatus, a selected flow of contaminants can be achieved. The flow is achieved due to the fact that vapor pressure of contaminants proximate the cooler portion of the apparatus will have a lower partial pressure than the contaminants above the warmer portion of the apparatus. In some embodiments, an average temperature gradient of at least 10 degrees Celsius per centimeter is achieved between the first portion and the second portion. In other embodiments, an average temperature gradient of at least 50 degrees Celsius per centimeter is achieved between the first portion and the second portion. In still other embodiments, an average temperature gradient of at least 80 degrees Celsius per centimeter is achieved.

Any suitable cooling agent providing any suitable temperature gradient can be used provided it can be managed within a system while maintaining the operation of the system. It will also be appreciated that it is the relative temperatures between a first portion and a second portion that are relevant, and rather than cooling one of the first portion and the second portion to generate the gradient, one of the first portion and the second portion could be heated to achieve a similar temperature gradient.

Shown in FIG. 3A is an apparatus 300 having contamination protection using thermophoretics according to aspects of the present invention for use in an extreme ultraviolet (EUV) actinic mask inspection system or an EUV lithographic system. In apparatus 300, at least one of the duct 310 and the optical component 320 are thermally coupled to a heat control unit 330, to maintain the duct at a lower temperature than the optical component to generate a thermal gradient. As a result, the contaminants are pushed toward and then adsorbed by duct 310. In some embodiments, the duct is thermally coupled to the heat control unit. In some embodiments, the heat control unit is a cooling apparatus adapted to maintain the duct at a cooler temperature than the optical component.

An apparatus having thermophoretic capabilities can be constructed similar to the duct described above with reference to FIGS. 1A and 1B, however, a portion of the apparatus connected to a heat control unit will typically be thermally conductive. A region surrounding the thermally conductive region may be non-thermally conductive or of a reduced thermal conductivity to thermally isolate the thermally conductive region.

Figure 3C:
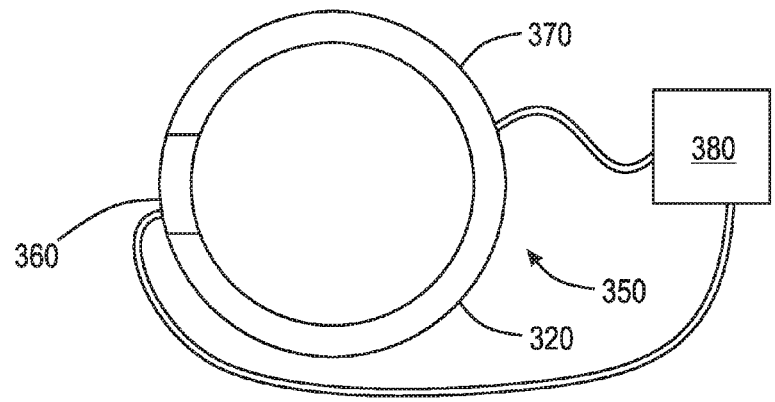
FIG. 3C is a top view of another example of an embodiment of an apparatus for use in an extreme ultraviolet (EUV) actinic mask inspection system or an EUV lithographic system, the apparatus having contamination protection including thermophoretic protection according to aspects of the present invention.

FIG. 3C is a top view of another example of an embodiment 350 of an apparatus for use in an extreme ultraviolet (EUV) actinic mask inspection system or an EUV lithographic system, the apparatus having contamination protection including thermophoretic protection according to aspects of the present invention.

As shown in FIG. 3C, in some embodiments, a first portion 360 of the duct is thermally coupled to a heat control unit 380, to maintain a temperature gradient between the first portion 360 of the duct and a second portion 370 of the duct. As a result, the contaminants are pushed toward and then adsorbed by the cooler of the first portion and the second portion.

Figure 4A:
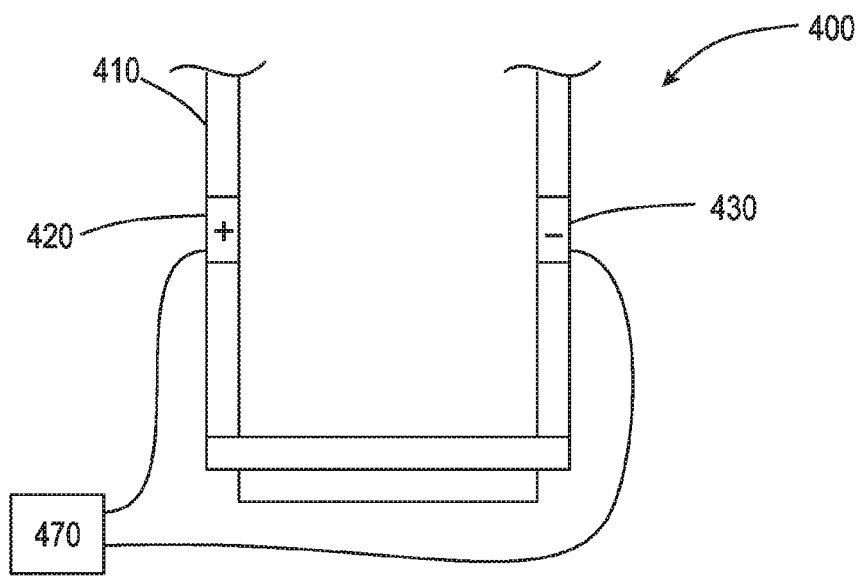
FIG. 4A is a partial schematic, cross-sectional diagram of an example of an embodiment of an apparatus for use in an extreme ultraviolet (EUV) actinic mask inspection system or an EUV lithographic system, the apparatus having contamination protection including electrostatic protection according to aspects of the present invention.
Figure 4B:
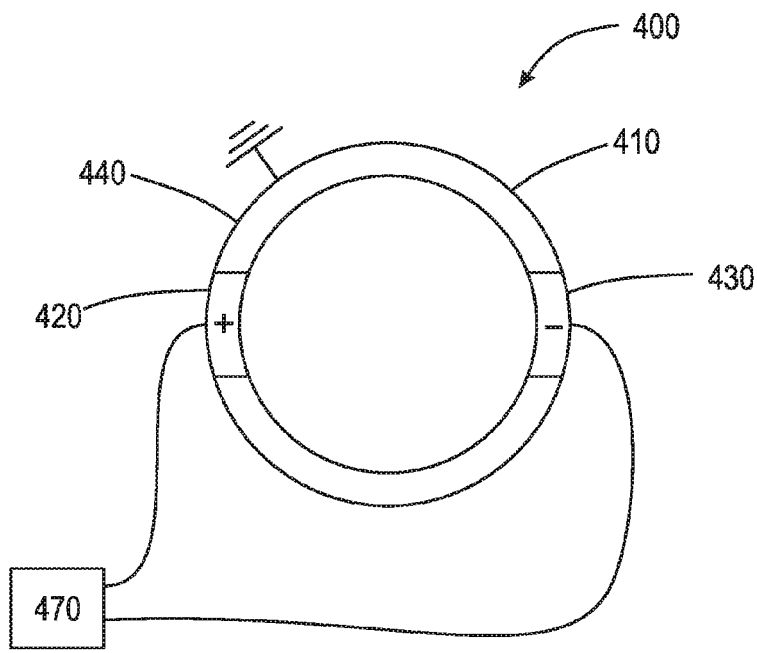
FIG. 4B is a top view of the apparatus of FIG. 4A.

FIG. 4A is a partial schematic, cross-sectional diagram of an example of an embodiment 400 of an apparatus for use in an extreme ultraviolet (EUV) actinic mask inspection system or an EUV lithographic system, the apparatus having contamination protection including electrostatic protection according to aspects of the present invention. FIG. 4B is a plan view of the apparatus of claim 4A.

The inventors have applied knowledge that EUV radiation is strongly ionizing resulting in a positive charge being generated on contaminants in duct 410 exposed to the EUV light, particularly for particles having a diameter greater than 5 nanometers. In apparatus 400, a voltage device 470 generates a voltage between a first portion 420 of the duct and a second portion 430 of the duct with a grounded insulative portion 440 therebetween. As a result, positively charged contaminants are drawn to the negatively charged second portion 430 thereby resulting in a ligation of contaminants.

While a gas is not needed to achieve electrostatic effects, apparatus having electrostatic capabilities may but need not have components need for a gas to flow as described above. Also, apparatus having electrostatic capabilities may but need not have components need for thermophoretics as described above. Portions of the apparatus described above described above with reference to FIGS. 1A, 1B, 2, 1A and 3B are omitted from FIGS. 4A and 4B to facilitate discussion.

Aspects of the invention have been described with reference to specific embodiments. It is obvious to a person skilled in the art, however, alterations and modifications can be made without leaving the scope of the subsequent claims.

What is claimed is:

1. An apparatus for use in an extreme ultraviolet (EUV) mask inspection system or an EUV lithographic system, the apparatus having contamination protection and comprising:
    a duct having a first end opening, a second end opening and an intermediate opening disposed intermediate the first end opening the second end opening;
    an optical component disposed so as 1) to receive EUV light from the first end opening after the light has passed through the second end opening or 2) to send light through the first end opening to the second end opening; and
    a source of low pressure gas at a first pressure, the gas having a high transmission of EUV light, fluidly coupled to the intermediate opening, the first end opening and the second end opening maintained at a lower pressure than the first pressure.

2. The apparatus of claim 1, wherein one of the duct and the optical component are thermally coupled to a heat control unit, to maintain the duct at a lower temperature than the optical component.

3. The apparatus of claim 2, wherein the duct is thermally coupled to the heat control unit, and the heat control unit is adapted to maintain the duct at a cooler temperature than the optical component.

4. The apparatus of claim 1, wherein a first portion of the duct is thermally coupled to a heat control unit, to maintain a temperature gradient between the first portion of the duct and a second portion of the duct.

5. The apparatus of claim 1, further comprising a gas permeable material disposed at the intermediate opening.

6. The apparatus of claim 1, wherein the intermediate opening is disposed closer to the first end opening than the second end opening.

7. The apparatus of claim 1, wherein the optical component comprises one of a mirror, a reticle, a sensor, a lens or a filter.

8. The apparatus of claim 1, wherein the optical component is disposed remote from the first end opening.

9. The apparatus of claim 1, wherein the low pressure gas has a transmission rate of greater than 70% for the EUV light.

10. The apparatus of claim 1, wherein the first pressure is less than 0.01 atmospheres.

11. The apparatus of claim 1, wherein the gas comprises molecular Hydrogen or Helium.

12. The apparatus of claim 1, wherein the length of the duct is at least two times greater than the maximum width dimension of a duct cross section.

13. The apparatus of claim 1, in a combination with at least one second duct having a second-duct first end opening, a second-duct second end opening and a second-duct intermediate opening,
    the second-duct intermediate opening disposed intermediate the second-duct first end opening and the second-duct second end opening;
    the optical component disposed so as 1) to receive light from the second-duct first end opening after the light has passed through the second-duct second end opening or 2) to send light through the second-duct first end opening to the second-duct second end opening; and
    a second-duct source of low pressure gas at a second-duct first pressure, the second-duct gas having a high transmission of EUV light, fluidly coupled to the second-duct intermediate opening, the second-duct first end opening and the second-duct second end opening maintained at a lower pressure than the second-duct first pressure.

14. The apparatus of claim 13, wherein the source of low pressure gas and the second-duct source of low pressure are the same source, and the gas and the second-duct gas are the same gas.

15. The apparatus of claim 1, further comprising a voltage device adapted to generate a voltage between a first portion of the duct and a second portion of the duct with a grounded electrically-insulative portion therebetween.

16. An apparatus for use in an extreme ultraviolet (EUV) mask inspection system or an EUV lithographic system, the apparatus having contamination protection and comprising:
    a duct having a first end opening, a second end opening and an intermediate opening disposed intermediate the first end opening the second end opening;
    an optical component disposed so as 1) to receive light from the first end opening after the light has passed through the second end opening or 2) to send light through the first end opening to the second end opening; and
    a heat control unit thermally coupled to the duct, the heat control unit being adapted to maintain the duct at a cooler temperature than the optical component.

17. The apparatus of claim 16, wherein an average temperature gradient between the duct and the optical component is at least 10 degrees Celsius per centimeter.

18. An apparatus for use in an extreme ultraviolet (EUV) mask inspection system or an EUV lithographic system, the apparatus having contamination protection and comprising:
    a duct having a first end opening, a second end opening and an intermediate opening disposed intermediate the first end opening the second end opening;
    an optical component disposed so as 1) to receive light from the first end opening after the light has passed through the second end opening or 2) to send light through the first end opening to the second end opening; and
a heat control unit thermally coupled to the duct,
    a first portion of the duct being thermally coupled to the heat control unit to maintain a temperature gradient between the first portion of the duct and a second portion of the duct.

19. The apparatus of claim 18, wherein an average temperature gradient between the first portion and the second portion is at least 10 degrees Celsius per centimeter.

20. The apparatus of claim 18, wherein the first portion and the second portion are disposed on opposing lateral sides of the duct.

21. An apparatus for use in an extreme ultraviolet (EUV) mask inspection system or an EUV lithographic system, the apparatus having contamination protection and comprising:
    a duct having a first end opening, and a second end opening;
    an optical component disposed so as 1) to receive light from the first end opening after the light has passed through the second end opening or 2) to send light through the first end opening to the second end opening; and
    a voltage device adapted to generate a voltage between a first portion of the duct and a second portion of the duct with a grounded insulative portion therebetween.

22. A method of contamination protection for use in an extreme ultraviolet (EUV) mask inspection system or an EUV lithographic system, comprising:
    flowing a low pressure gas at a first pressure in a duct having A) a first end opening and a second end opening and B) an intermediate opening disposed intermediate the first end opening and the second end opening, the gas flowing into the duct through the intermediate opening;

maintaining the first end opening and the second end opening at a lower pressure than the first pressure; and projecting EUV light through the duct, the EUV light A) traveling from the first end opening then through the second end opening to an optical element or B) traveling from the optical component, then through the first end opening to the second end opening, the gas having a high transmission of EUV light.

23. The method of claim 22, wherein the optical component comprises one of a mirror, a reticle, a sensor, a lens or a filter.

24. The method of claim 22, wherein the optical component is disposed remote from the second end opening.

25. The method of claim 22, wherein the low pressure gas has a transmission rate greater than 70% for the EUV light.

26. The method of claim 22, wherein the first pressure is less than 0.01 atmospheres.

27. The method of claim 22, wherein the gas comprises molecular Hydrogen or Helium.

28. A method of contamination protection for use in an extreme ultraviolet (EUV) mask inspection system or an EUV lithographic system, comprising:

maintaining a voltage difference between a first portion of a duct and a second portion of the duct with a grounded insulative portion disposed between the first portion and the second portion, the duct having A) a first end opening and a second end opening, the first portion and the second portion both being disposed between the first end opening and the second end opening; and projecting EUV light through the duct, the EUV light 1) traveling from the first end opening then through the second end opening to an optical element or 2) traveling from the optical component, then through the first end opening to the second end opening.

29. The method of claim 28, further comprising providing a gas in the duct, the gas having a high transmission of EUV light.

* * * * *